United States Patent [19]

Ohnishi

[11] Patent Number: 4,618,664

[45] Date of Patent: Oct. 21, 1986

[54] PULLULAN COPOLYMER

[75] Inventor: Yasuhiko Ohnishi, Seto, Japan

[73] Assignee: Sadayoshi Kamiya, Nagoya, Japan; a part interest

[21] Appl. No.: 689,928

[22] Filed: Jan. 9, 1985

[30] Foreign Application Priority Data

Jan. 9, 1984 [JP] Japan ................................ 59-002345

[51] Int. Cl.$^4$ ........................ C08G 89/00; C08F 36/00
[52] U.S. Cl. .................................... 527/300; 527/312; 527/313; 527/314; 527/315; 523/109; 351/160 R
[58] Field of Search ............... 524/300, 311, 312, 313, 524/314, 315; 523/109; 106/35; 526/238.2; 351/160 R, 160 H; 3/1

[56] References Cited

U.S. PATENT DOCUMENTS 3,912,591 10/1975 Kato et al.
4,029,616 6/1977 Nakashio et al. .................... 524/732
4,280,937 7/1981 Bartl et al. .......................... 527/314

OTHER PUBLICATIONS

Wallenfels et al, Untersuchungen an Pullulan, Biochemische Zeitschrift, vol. 341, pp. 443–450 (1965).
Kirk-Othmer Encyclopedia of Chemical Technology, 3rd Edition (Wiley 1978–84) vol. 9, pp. 198 and 218, vol. 12, p. 62 and vol. 15, p. 455.

Primary Examiner—Harold D. Anderson
Assistant Examiner—Nathan M. Nutter
Attorney, Agent, or Firm—Spencer & Frank

[57] ABSTRACT

A pullulan copolymer obtained by reacting with a polymerizable olefinic compound a pullulan ester which is produced by reacting pullulan with an unsaturated acid to introduce a double bond of carbon thereinto. It is highly hydrophilic and is a material having a high affinity for a living body and which is, therefore, useful for making contact lenses, intraocular lenses, artificial bones and blood vessels, etc.

4 Claims, 1 Drawing Figure

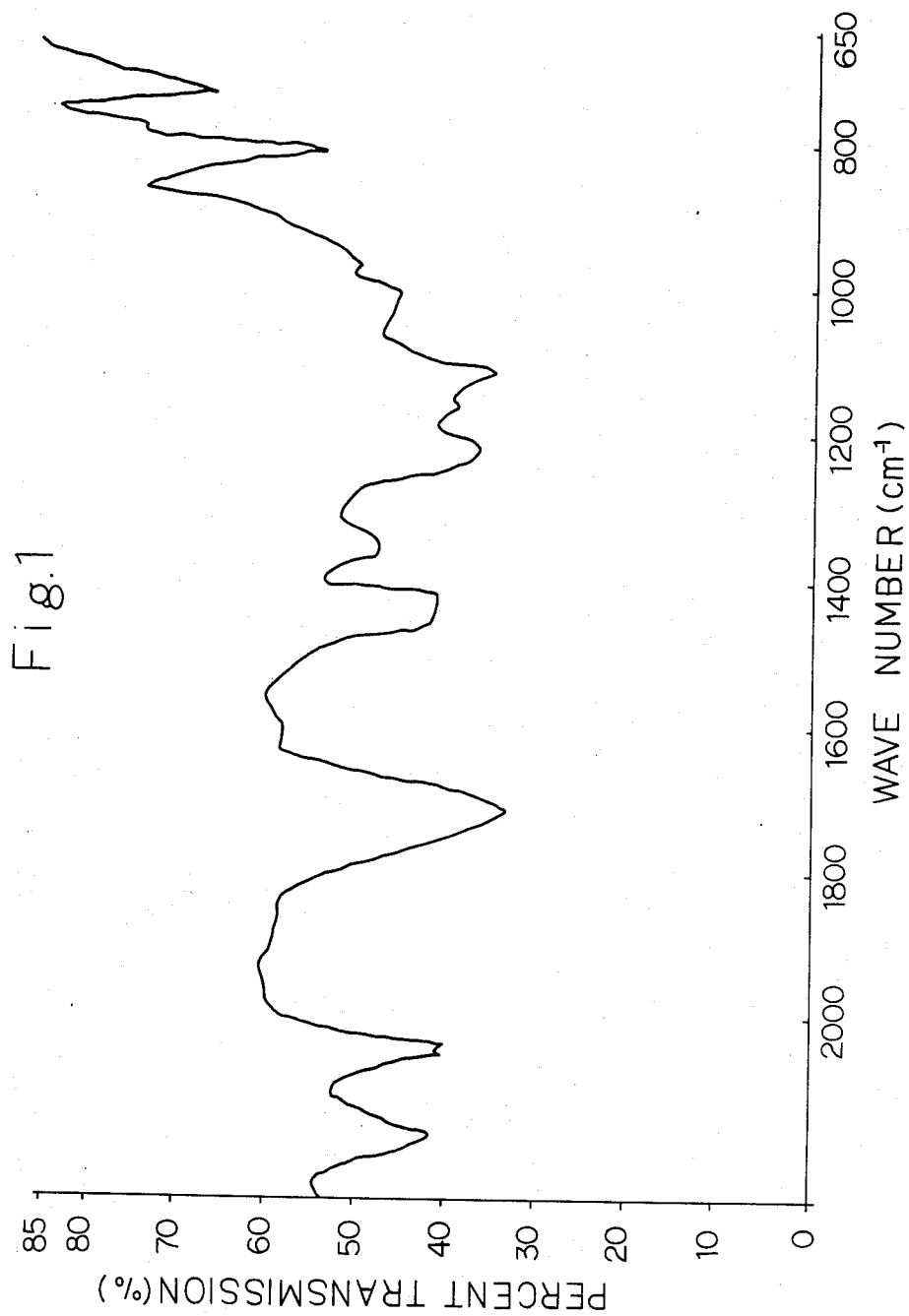

PULLULAN COPOLYMER

BACKGROUND OF THE INVENTION

This invention relates to a novel pullulan copolymer.

The term "pullulan" as herein used refers to linear polysaccharides having $\alpha(1\rightarrow 6)$, $\alpha(1\rightarrow 4)$ glycoside bonds and containing maltotriose as a recurring unit.

The inventor of this invention has found that the industrial production of pullulan having an appropriate molecular weight can be realized at a low cost by fermentation and as a result of his extensive efforts to develop a functional high molecular material, he has succeeded in developing a novel high molecular material having a skeleton of pullulan.

SUMMARY OF THE INVENTION

The pullulan copolymer of this invention is obtained by reacting with a polymerizable olefin compound a pullulan ester which is produced by reacting pullulan with an unsaturated acid to introduce a double bond of carbon thereinto.

If a vinyl monomer having various kinds of functional groups is used, therefore, it is possible to obtain a functional high polymer having a variety of functions. The pullulan copolymer of this invention is highly hydrophilic, as it has a skeleton of pullulan. It is, therefore, a useful material having a high affinity for a living body and can, for example, be advantageously used for dental application or for making contact or Intraocular lenses or artificial bones or blood vessels. It is also useful to form a film which can be used to make a membrane for ultrafiltration or an electron beam resist.

BRIEF DESCRIPTION OF THE DRAWING

FIG. 1 is a diagram showing the infrared absorption spectra of a pullulan ester-methyl methacrylate copolymer according to EXAMPLE 1 of this invention.

DESCRIPTION OF THE PREFERRED EMBODIMENT

The pullulan copolymer of this invention can be produced by two steps as will hereinafter be described. I. Pullulan is reacted with an unsaturated acid so that a double bond may be introduced thereinto. More specifically, pullulan is reacted with an unsaturated acid of the formula $HOOCR^{10}$, in which $R^{10}$ is an unsaturated hydrocarbon group having a $>C=C<$ bond and 2 to 16 carbon atoms or anhydride thereof, in the presence of a saturated acid of the formula $HOOCR^{11}$, in which $R^{11}$ is an alkyl group having 1 to 14 carbon atoms, or an anhydride thereof and an acid catalyst. Alternatively, pullulan is reacted with an unsaturated acid of the formula $HOOCR^{10}$, in which $R^{10}$ is an organic group having a $>C=C<$ bond and 2 to 16 carbon atoms, or an anhydride thereof in the presence of a saturated acid or an anhydride of a saturated acid of the formula $HOOCR^{11}$, in which $R^{11}$ is an alkyl group having 1 to 14 carbon atoms, and a basic catalyst. As a result, there is obtained a pullulan olefin ester of the formula (A):

$$[C_6H_7O_2(OH)_{3-a-b}(OX)_a(OY)_b]_m H_2O \quad (A)$$

where

X: $-C(=O)R^1$ ($R^1$ is an unsaturated hydrocarbon group derived from an unsaturated acid and having a double bond and 2 to 16 carbon atoms);

Y: $-C(=O)R^2$ ($R^2$ is an alkyl group having 1 to 14 carbon atoms); and m: 5 or a larger natural number.

II. The ester is reacted with a polymerizable olefinic compound to produce a pullulan copolymer. This reaction may be carried out in a solvent in which both of the ester and the olefinic compound are well soluble, such as acetone. Alternatively, the ester can be directly dissolved or dispersed in the olefinic compound.

The polymerizable olefinic compound is a compound which can form the recurring units shown in the parentheses in the formula (B) upon polymerization:

$$-C(R^3)R^4-C(R^5)R^6-_n \quad (B)$$

where $R^3$, $R^4$, $R^5$: hydrogen or $CH_3$;

$R^6$: $-C(=O)OR^7$, $-C(=O)CN$, $-OH$, or an acyloxy, phenyl, pyridine, tolyl, pyrrolidone, lower alkyl or substituted pyrrolidone group; and n: a natural number of 20 to 300,000.

$R^7$ is an alkyl group having 1 to 12 carbon atoms, a cyclohexyl group, a hydroxylalkyl group having 1 to 4 carbon atoms, an aminoalkyl group having 1 to 8 carbon atoms, a dialkyl aminoalkyl group having 1 to 8 carbon atoms, a glycidyl group, a tetrahydrofuran group, a lower alkyl substituted tetrahydrofuran group having 1 to 4 carbon atoms, a benzyl group, a polyethylene oxide group having a polymerization degree of 2 to 11 and an imino group.

Specific examples of the polymerizable olefinic compound include the alkyl ester, cyclohexyl ester, 2-hydroxyethyl ester, 2-hydroxypropyl ester, 2-hydroxybutyl ester, acrylamide, methacrylamide, acryl- or methacryldimethylamide or benzyl ester of an $\alpha,\beta$-unsaturated acid, such as acrylic or methacrylic acid, the aminoalkyl ester having 1 to 3 carbon atoms, dialkylaminoalkyl ester having 1 to 3 carbon atoms, glycidyl ester, polyethylene glycol monoester, tetrahydrofurfuryl ester, acrylonitrile, methacrylonitrile or other nitrile compound of any such acid, vinyl, methylvinyl or dimethylvinyl alcohol, vinyl acetate, propionate or butylate or other alkyl ester of vinyl or methylvinyl alcohol having 1 to 3 carbon atoms, styrene, methylstyrene, vinyltoluene, vinylpyridine, vinylpyrrolidone and vinylmethylpyrrolidone.

The polymerization may be initiated by employing an ordinary radical polymerization initiator, such as azobisisobutylnitrile (AIBN), benzoyl peroxide (BPO) or t-butylhydroperoxide. The amount of the initiator may be appropriately selected, but is usually from about 0.1% to about 5% by weight.

The pullulan copolymer of this invention is hardly soluble in any organic solvent, such as acetone, dioxane, chloroform or dimethylformamide, at a temperature of 40° C. It is very hard and often has a Rockwell hardness of 150 on the M scale.

The pullulan copolymer of this invention can be formed in any desired shape by bulk polymerization if an appropriately shaped mold is employed. The ratio of the polymers of formulas (A) and (B) can be varied to suit the purpose for which the copolymer will be used. The pullulan copolymer of this invention is, therefore, very useful for making contact or intraocular lenses, or artificial blood vessels, bones or corneas, beds for artificial teeth, or other artificial organs. Referring particularly to a hard contact lens, it is preferable to use a material prepared from a methacrylic acid alkyl ester.

The polymers of formulas (A) and (B) preferably have a ratio of 1 to 40. The solubility of a pullulan ester in a methacrylic acid ester is important for bulk polymerization. An ester prepared from pullulan and a mixture of, for example, acetic acid, methacrylic acid and acrylic acid preferably contains 10 to 40% of acetic acid and 5 to 20% of the other unsaturated acids. The bulk polymer thus obtained in the shape of a sheet or bar can be cut, polished and beveled to provide a good contact lens.

A contact lens formed from a pullulan-methyl methacrylate copolymer was compared with a contact lens formed from poly(methyl methacrylate). A patient for whom the conventional poly(methyl methacrylate) lens became unusable soon because of the eyes becoming blood shot when fitted could wear the lens formed from the copolymer of this invention for eight hours continuously without giving rise to any problem. The lens showed a better degree of wearing comfort with an increase in wet. This was particularly true with a lense having its surface treated with, for example, an alcoholic alkali.

A hydrogel having a high water absorbing power is formed if a pullulan ester is copolymerized with a hydroxyalkyl methacrylate, such as 2-hydroxyethyl methacrylate (HEMA). A pullulan-HEMA copolymer having a pullulan to HEMA ratio of 1:5 and formed in the shape of a bar was cut, polished and beveled to form a contact lens and the lens was heated in boiling water for 10 minutes. There was obtained a soft contact lens which was good in mechanical properties, such as tensile strength and elasticity. This hydrogel is useful for making a good support for medicines.

The invention will now be described more specifically with reference to several examples thereof.

EXAMPLE 1

A mixture containing 130 g of acetic anhydride, 370 g of methacrylic acid, 100 g of acrylic acid, 20 g of potassium acetate, 1.6 g of hydroquinone and 500 g of dimethylformamide was heated at 118° C. for 10 minutes, while it was being stirred. After the mixture had been cooled, 20 g of pullulan treated with a saturated potassium acetate solution and having an average molecular weight of 60,000 were dissolved in the mixture. The solution was stirred carefully and heated at 118° C. for 30 minutes. After the reaction product had been cooled, it was introduced into three times as much water and a white precipitate was separated by filtration. The precipitate was dissolved in acetone and the solution was subjected to filtration. The filtrate was injected into water and a sediment was collected. This sequence of procedure was repeated three times. The sediment was dried at a reduced pressure to yield 6 g of a white pullulan ester powder. The ester was soluble in acetone, chloroform, dimethylformamide, methyl methacrylate, etc., swelled with benzene and toluene and was insoluble in water, methanol and formamide. It contained 31% of acetic acid, 10% of methacrylic acid and 8% of acrylic acid.

Five grams of the pullulan ester were dissolved in 15 g of methyl methacrylate and 0.1 g of azobisisobutylnitrile was added to the solution. The solution was put in a glass tube having a diameter of 15 mm, and the tube was degassed carefully and closed tightly. The solution was reacted for polymerization at 40° C. for 24 hours and the tube was, then, heated in an air bath at 100° C. for three hours, whereby a polymer in the shape of a bar was formed.

After the tube had been cooled, the polymer was removed from the tube and annealed in an air bath at 80° C. for 24 hours to yield 19 g of a bulk polymer. The polymer was hardly soluble in any organic solvent such as acetone, chloroform or formamide, methanol or water. It had a Vicat softening temperature of 165° C. (ASTM D1525) and a Rockwell hardness (M scale) of 100 (ASTM D785).

FIG. 1 shows the infrared absorption spectra of the copolymer. The spectra do not include any absorption due to the double carbon bond at 1635 cm$^{-1}$. The fact that the product was insoluble in any organic solvent, water, etc. confirmed that it was a copolymer.

EXAMPLE 2

A mixture containing 410 g of methacrylic acid, 135 g of acetic anhydride, 20 g of potassium acetate, 500 g of dimethylformamide and 1 g of hydroquinone was heated at 115° C. for 12 minutes, while it was being stirred. Twenty grams of the pullulan used in EXAMPLE 1, which had been treated with a saturated potassium acetate solution, were dissolved in the mixture and the solution was heated at 118° C. for 30 minutes. After the reaction product had been cooled, it was introduced into three times as much water and the procedure of EXAMPLE 1 was repeated to yield 14 g of a white powder. It contained 31.2% of acetic acid and 18.0% of methacrylic acid. It was insoluble in water and methanol, and soluble in acetone and dioxane.

Five grams of the mixed acetic and methacrylic pullulan ester were mixed with 30 g of methyl methacrylate and 0.1 g of azobisisobutylnitrile was added to the mixture. The procedure of EXAMPLE 1 was thereafter repeated for polymerization in a glass tube to yield 34 g of a bulk polymer in the shape of a bar. It was insoluble in water and methanol and also in acetone, dioxane and chloroform. It had a Rockwell hardness (M scale) of 100 and a Vicat softening temperature of 165° C.

EXAMPLE 3

The procedure of EXAMPLE 2 was repeated for esterification, except that 410 g of acrylic were used instead of methacrylic acid. There were obtained 12 g of a white powder. It contained 28.0% of acetic acid and 14.6% of acrylic acid. It was insoluble in water and methanol, but soluble in acetone and dioxane. The procedure of EXAMPLE 1 was repeated for copolymerizing of 20 g of methyl methacrylate onto 5 g of the mixed acetic and acrylic pullulan ester to yield 24 g of a bulk polymer in the shape of a bar. It was insoluble in water, methanol, dioxane and chloroform. It had a Rockwell hardness of 100 and a Vicat softening temperature of 165° C.

EXAMPLE 4

A mixture containing 400 g of acrylic acid, 130 g of acetic anhydride, 90 g of potassium acetate, 490 g of toluene and 1 g of hydroquinone was heated at 115° C. for 12 minutes, while it was being stirred. Then, 20 g of the pullulan treated with a saturated potassium acetate solution and used in EXAMPLE 1 were dissolved in the mixture. The solution was reacted at 118° C. for 35 minutes, while it was being stirred carefully. After the reacted solution had been cooled, it was introduced into water and lumps of ice were added thereinto. A caustic soda solution was added to the solution to raise its pH value to 5.0. The principal product was collected, washed with a lot of water carefully and subjected to filtration. The filtrate was dried at a reduced pressure to yield 11 g of a white powder. The mixed acetic and acrylic pullulan ester thus obtained contained 21% of acetic acid and 10.9% of acrylic acid. It was insoluble in water and methanol, but soluble in dioxane and chloroform.

Five grams of the ester were dissolved in 600 ml of dioxane. Fifty grams of methyl methacrylate were added to the solution, while nitrogen gas was being introduced thereinto, and 0.6 g of benzoyl peroxide was also added. The solution was reacted at 70° C. for 10 hours. After the reaction product had been cooled, it was introduced into three times as much methanol and the sediment was collected by filtration. It was dried at a reduced pressure and the dried material was extracted by a Soxhlet apparatus. The residue was dried at a reduced pressure to yield 40 g of a white product. It was insoluble in water, methanol, and formamide.

EXAMPLE 5

Five grams of the ester obtained in EXAMPLE 1 were dissolved in 50 g of 2-hydroxyethyl methacrylate, and 0.25 g of azobisisobutylonitrile was added to the solution to initiate its polymerization in a glass tube as in EXAMPLE 1. The polymerization was carried out at a temperature of 50° C. for 24 hours. The tube was, then, heated at 80° C. for two hours and a polymer was removed from the tube. It was annealed at 100° C. for four hours in a drier to yield a hydrophilic product. It had a Rockwell hardness (M scale) of 100, a Vicat softening temperature of 115° C. and a water absorbing ratio of 20%.

EXAMPLE 6

The bulk polymer in the shape of a bar as obtained in EXAMPLE 1 was cut by a lathe rotating at 2000 rpm and convex and concave surfaces each having a predetermined radius of curvature were formed at the same rotating speed. The product was fitted in a pit dish on a lens polisher and polished by an upper member rotating at 15 rpm and a lower member rotating at 200 rpm. The polished product was beveled by a beveling machine to yield a contact lens. The lens was treated with an alcoholic alkali to obtain a hydrophilic surface and showed a good hydrophilicity at a contact angle of 49°.

The lens was tested with a power of −5.50 for a person whose eyes had both a sight of 0.01 (1.0×S−5.50) and who could not withstand any conventional poly(methylmethacrylate) lens. He could continue wearing the lens for eight hours. The lens gave a sight of 1.0 to both of his eyes. After he had used the lens for a year, the base curve and power of the lens were examined, but did not reveal any change. The details of the lens were as follows:

|  | Base curve | Power | Size |
| --- | --- | --- | --- |
| Left eye | 740 mm | −5.50 | 8.8 mm |
| Right eye | 745 mm | −5.50 | 8.8 mm |

What is claimed is:

1. A pullulan copolymer obtained by reacting pullulan with an unsaturated acid of the formula HOOCR$^{10}$ or the anhydride thereof in which R$^{10}$ is an unsaturated hydrocarbon group having a carbon-carbon double bond and 2 to 16 carbon atoms, in the presence of a saturated acid of the formula HOOCR$^{11}$ in which R$^{11}$ is an alkyl group having 2 to 16 carbon atoms and an acid catalyst to produce a pullulan olefin ester of formula (A):

$$[C_6H_7O_2(OH)_{3-a-b}(OX)_a(OY)_b]_m H_2O \qquad (A)$$

where

X is —C(=O)R$^1$ and R$^1$ is an unsaturated hydrocarbon group derived from an unsaturated acid and having a carbon-carbon double bond and 2 to 16 carbon atoms, Y is —C(=O)R$^2$ and R$^2$ is an alkyl group having 1 to 14 carbon atoms, m is a natural number of at least 5, and a and b each is a natural number defined by a+b≦3 and copolymerizing said pullulan olefinic ester with an olefinic compound polymerizable to form a recurring unit of formula (B):

$$[C(R^3)R^4—C(R^5)R^6]_n \qquad (B)$$

where

R$^3$, R$^4$ and R$^5$ are each selected from hydrogen and CH$_3$;

R$^6$ is selected from —C(=O)OR$^7$, —C(=O)CN, —OH, acyloxy, phenyl, pyridine, tolyl, pyrrolidone, lower alkyl and substituted pyrrolidone groups, R$^7$ being selected from an alkyl group having 1 to 12 carbon atoms, a cyclohexyl group, a hydroxyalkyl group having 1 to 4 carbon atoms, an aminoalkyl group having 1 to 8 carbon atoms, a dialkyl aminoalkyl group having 1 to 8 carbon atoms, a glycidyl group, a tetrahydrofuran group, a lower alkyl substituted tetrahydrofuran group having 1 to 4 carbon atoms, a benzyl group, a polyethylene oxide group having a polymerization degree of 2 to 11 and an imino group; and n is a natural number of 20 to 300,000.

2. A contact lens formed from the pullulan copolymer of claim 1.

3. A pullulan copolymer obtained by reacting pullulan with an unsaturated acid of the formula HOOCR$^{10}$ or the anhydride thereof in which R$^{10}$ is an unsaturated hydrocarbon group having a carbon-carbon double bond and 2 to 16 carbon atoms, in the presence of a saturated acid of the formula HOOCR$^{11}$ in which R$^{11}$ is an alkyl group having 1 to 14 carbon atoms and an basic catalyst to produce a pullulan olefin ester of formula (A):

$$[C_6H_7O_2(OH)_{3-a-b}(OX)_a(OY)_b]_m H_2O \qquad (A)$$

where

X is —C(=O)R$^1$ and R$^1$ is an unsaturated hydrocarbon group derived from an unsaturated acid and having a carbon-carbon double bond and 2 to 16 carbon atoms, Y is —C(=O)R$^2$ and R$^2$ is an alkyl group having 1 to 14 carbon atoms, m is a natural number of at least 5, and a and b each is a natural number defined by a+b≦3 and copolymerizing said pullulan olefinic ester with an olefinic compound polymerizable to form a recurring unit of formula (B):

$$[C(R^3)R^4—C(R^5)R^6]_n \qquad (B)$$

where $R^3$, $R^4$ and $R^5$ are each selected from hydrogen and $CH_3$;

$R^6$ is selected from $-C(=O)OR^7$, $-C(=O)CN$, $-OH$, acyloxy, phenyl, pyridine, tolyl, pyrrolidone, lower alkyl and substituted pyrrolidone groups, $R^7$ being selected from an alkyl group having 1 to 12 carbon atoms, a cyclohexyl group, a hydroxyalkyl group having 1 to 4 carbon atoms, an aminoalkyl group having 1 to 8 carbon atoms, a dialkyl aminoalkyl group having 1 to 8 carbon atoms, a glycidyl group, a tetrahydrofuran group, a lower alkyl substituted tetrahydrofuran group having 1 to 4 carbon atoms, a benzyl group, a polyethylene oxide group having a polymerization degree of 2 to 11 and an imino group; and n is a natural number of 20 to 300,000.

4. A contact lens formed from the pullulan copolymer of claim 3.

* * * * *